(12) United States Patent
Hart et al.

(10) Patent No.: US 9,981,267 B2
(45) Date of Patent: May 29, 2018

(54) PAIRED LASER AND ELECTROKINETIC SEPARATION, MANIPULATION, AND ANALYSIS DEVICE

(71) Applicant: The Government of the United States of America, as represented by the Secretary of the Navy, Washington, DC (US)

(72) Inventors: Sean J. Hart, Keswick, VA (US); Sarah J. R. Staton, Washington, DC (US); Alexander V. Terray, Alexandria, VA (US); Gregory E. Collins, Huntingtown, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 51 days.

(21) Appl. No.: 15/183,531

(22) Filed: Jun. 15, 2016

(65) Prior Publication Data
US 2016/0332161 A1 Nov. 17, 2016

Related U.S. Application Data

(62) Division of application No. 14/043,384, filed on Oct. 1, 2013, now Pat. No. 9,731,293.
(Continued)

(51) Int. Cl.
*B01L 3/00* (2006.01)
*G01N 1/10* (2006.01)
(Continued)

(52) U.S. Cl.
CPC ... *B01L 3/502761* (2013.01); *B01L 3/502715* (2013.01); *B01L 3/502784* (2013.01);
(Continued)

(58) Field of Classification Search
CPC ............... B03C 5/02; B01L 3/00; G01N 1/10
(Continued)

(56) References Cited

U.S. PATENT DOCUMENTS

| 6,251,691 B1* | 6/2001 | Seul | B01J 19/0046 |
| | | | 204/400 |
| 2009/0032449 A1* | 2/2009 | Mueth | G02B 21/32 |
| | | | 210/94 |

(Continued)

*Primary Examiner* — Brian J. Sines
(74) *Attorney, Agent, or Firm* — US Naval Research Laboratory; Roy Roberts

(57) ABSTRACT

The combined value of integrating optical forces and electrokinetics allows for the pooled separation vectors of each to be applied, providing for separation based on combinations of features such as size, shape, refractive index, charge, charge distribution, charge mobility, permittivity, and deformability. The interplay of these separation vectors allow for the selective manipulation of analytes with a finer degree of variation. Embodiments include methods of method of separating particles in a microfluidic channel using a device comprising a microfluidic channel, a source of laser light focused by an optic into the microfluidic channel, and a source of electrical field operationally connected to the microfluidic channel via electrodes so that the laser light and the electrical field to act jointly on the particles in the microfluidic channel. Other devices and methods are disclosed.

4 Claims, 18 Drawing Sheets

Related U.S. Application Data

(60) Provisional application No. 61/709,290, filed on Oct. 3, 2012.

(51) Int. Cl.
    *B03C 5/02*         (2006.01)
    *B81B 7/02*         (2006.01)
    *G01N 15/10*       (2006.01)

(52) U.S. Cl.
    CPC ......... *B81B 7/02* (2013.01); *B01L 2200/0652* (2013.01); *B01L 2300/0864* (2013.01); *B01L 2400/0418* (2013.01); *B01L 2400/0421* (2013.01); *B01L 2400/0424* (2013.01); *B01L 2400/0454* (2013.01); *B01L 2400/0487* (2013.01); *G01N 2015/1081* (2013.01)

(58) Field of Classification Search
    USPC ........... 204/547; 422/68.1, 81, 82, 502, 503, 422/504, 509, 521; 436/43, 174, 177, 436/180
    See application file for complete search history.

(56) References Cited

U.S. PATENT DOCUMENTS

2011/0030808 A1*   2/2011   Chiou ............... B01L 3/502738
                                                          137/13
2012/0315690 A1*  12/2012  Di Carlo ................ G01N 15/10
                                                          435/287.1

* cited by examiner

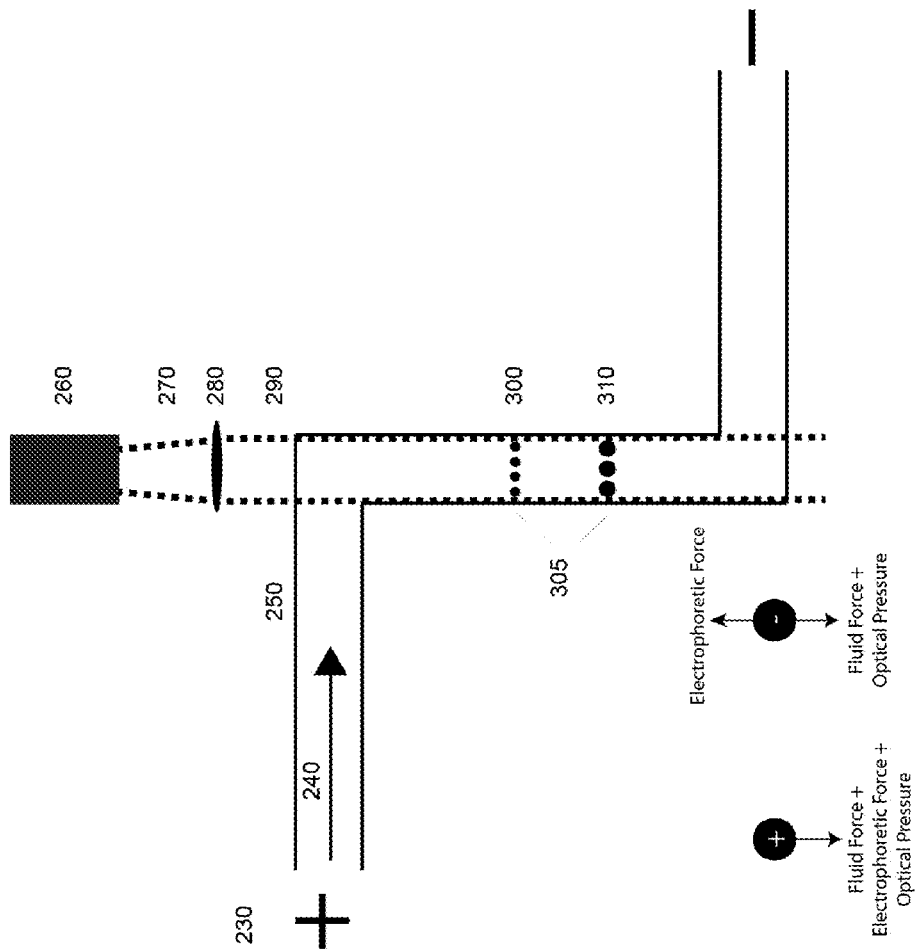

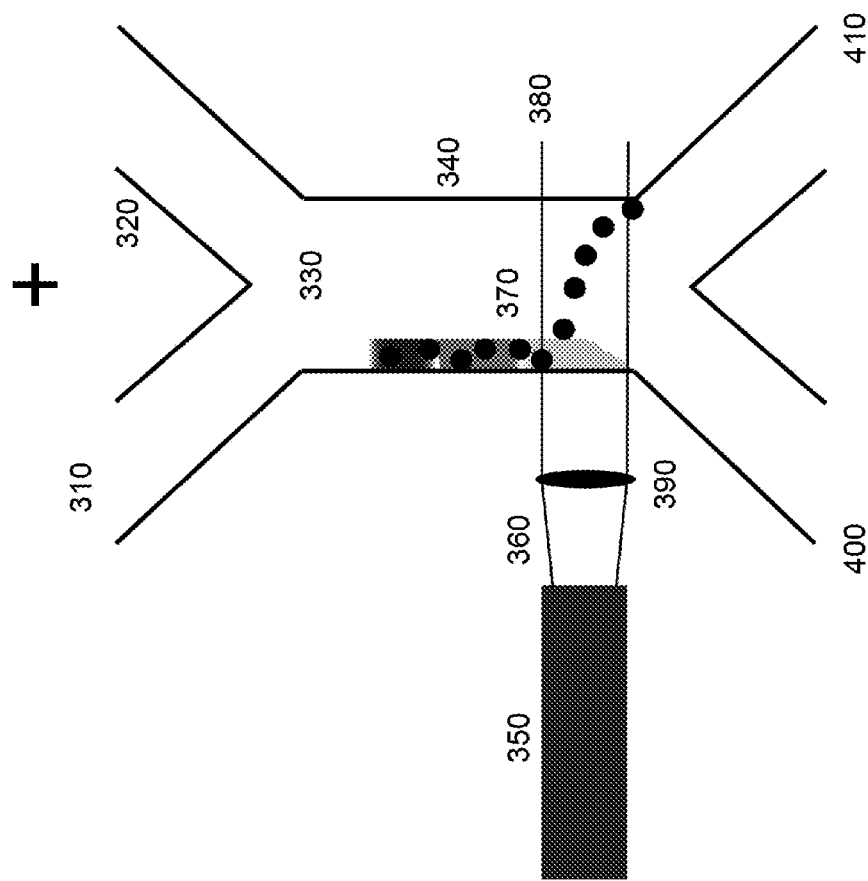

Side view

Cross-sectional view

PAIRED LASER AND ELECTROKINETIC SEPARATION, MANIPULATION, AND ANALYSIS DEVICE

CROSS-REFERENCE TO RELATED APPLICATIONS

This Application claims the benefit as a divisional of U.S. patent application Ser. No. 14/043,384 filed on Oct. 1, 2013, which in turn claims the benefit of U.S. Provisional Application 61/709,290 filed on Oct. 3, 2012, the entirety of each of which is incorporated herein by reference.

BACKGROUND

A need exists for techniques for manipulation of analytes in liquids.

BRIEF SUMMARY

In one embodiment, a method of separating particles in a microfluidic channel includes providing a device comprising a microfluidic channel, a source of laser light focused by an optic into the microfluidic channel, and a source of electrical field operationally connected to the microfluidic channel via electrodes; flowing particles in a liquid through the microfluidic channel; and manipulating the laser light and the electrical field to act jointly on the particles in the microfluidic channel, thereby separating the particles based on size, shape, refractive index, electrical charge, electrical charge distribution, charge mobility, permittivity, and/or deformability.

In another embodiment, a method of separating particles in a microfluidic channel includes a providing a device comprising a central microfluidic channel operably connected to a first inlet and a second inlet and a first outlet and a second outlet, and a source of laser light focused by an optic into the central microfluidic channel in a direction orthogonal to the central microfluidic channel; flowing particles and molecular species together in a first liquid through the first inlet while flowing a second liquid through the second inlet so as to pinch the flow from the first inlet; and applying optical force from the source of laser light to separate the particles from the molecular species such that the molecular species tend to exit the first outlet and the particles tend to exit the second outlet.

In a further embodiment, a method of separating particles in a microfluidic channel includes providing a device comprising a microfluidic channel comprising an inlet and a plurality of exits, and a source of laser light focused by an optic to cross the microfluidic channel at an angle; flowing a plurality of particles in a liquid through the inlet into the microfluidic channel; and selecting the angle of the laser light so as to produce an optical force on the particles while maximizing residence time in the laser light of selected particles, thus selectively separating the particles into the plurality of exits.

In yet another embodiment, a method of separating particles in a microfluidic channel includes providing a device comprising a microfluidic channel configured to supply a dielectrophoretic (DEP) field to an interior of the channel via a (1) DEP electrode system or (2) insulator DEP system having shaped wall geometry or obstruction geometry, and a source of laser light focused by an optic into the microfluidic channel; flowing a plurality of particles in a liquid into the microfluidic channel; and operating the laser light and DEP field jointly on particles in the microfluidic channel to trap the particles or modify their velocity, wherein said DEP field is linear or non-linear.

In a still further embodiment, a method of separating particles in a microfluidic channel includes providing a device comprising a microfluidic channel configured to supply a linear or non-linear dielectrophoretic (DEP) field to an interior of the channel via a (1) DEP electrode system or (2) insulator DEP system having shaped wall geometry or obstruction geometry; flowing a plurality of particles in a liquid into the microfluidic channel; and operating the DEP field on particles in the microfluidic channel to change velocity of the particles, wherein said DEP field is linear or non-linear.

An embodiment of a device includes a microfluidic channel comprising an inlet and a plurality of exits, and a source of laser light focused by an optic to cross the microfluidic channel at a critical angle matched to velocity of flow in the microfluidic channel so as to produce an optical force on the particles while maximizing residence time in the laser light of selected particles, thus separating the particles into the plurality of exits, wherein the laser light is operable to apply forces to particles flowing through the microfluidic channel, thereby separating the particles into the plurality of exits.

Another embodiment of a device includes a microfluidic channel configured to supply a linear or non-linear dielectrophoretic (DEP) field to an interior of the channel via a (1) DEP electrode system or (2) insulator DEP system having shaped wall geometry or obstruction geometry, and a source of laser light focused by an optic into the microfluidic channel, wherein the laser light and DEP field operate jointly on particles in the microfluidic channel to trap the particles or modify their velocity.

A further embodiment of a device includes a microfluidic channel configured to supply a linear or non-linear dielectrophoretic (DEP) field to an interior of the channel via a (1) DEP electrode system or (2) insulator DEP system having shaped wall geometry or obstruction geometry, wherein DEP field operates on particles in the microfluidic channel to change velocity of the particles.

BRIEF DESCRIPTION OF THE DRAWINGS

FIG. 3 illustrates an embodiment wherein laser force is co-directional with fluid flow.

FIGS. 4A through 4E illustrate embodiment having laser force orthogonal to fluidic flow. FIG. 4A shows a general schematic of continuous separation. FIG. 4B illustrates the stage of sample introduction, with FIG. 4C showing a stage of a gated mode of operation with injection of a plug of charged molecular species and particles. FIG. 4D illustrates the beginning of separation of molecular species from particles and sub-populations of molecular species from each other during gated operation, with FIG. 4E showing a moment later when such separation is complete.

FIG. 8A shows a side of a DEP trap while FIG. 8B shows a cross-sectional view.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Description

The combined value of integrating optical forces and electrokinetics allows for the pooled separation vectors of each to be applied, providing for separation based on combinations of features such as size, shape, refractive index, charge, charge distribution, charge mobility, permittivity, and deformability. The interplay of these separation vectors allow for the selective manipulation of analytes with a finer degree of variation. Thus, the larger portfolio of separation vectors permits the probing of chemical composition, geometry, and internal structure of analytes. In concert optical forces and electrokinetics can both generate bulk fluid flow, e.g. electroosmotic flow, while also providing a means of physically separating both particulate and molecular species analyte mixtures, e.g. electrophoresis and dielectrophoresis. The technique also expands the separation and manipulation of particulate and molecular species by working without having to apply tag molecules to either type.

Experimental

Figure 1:
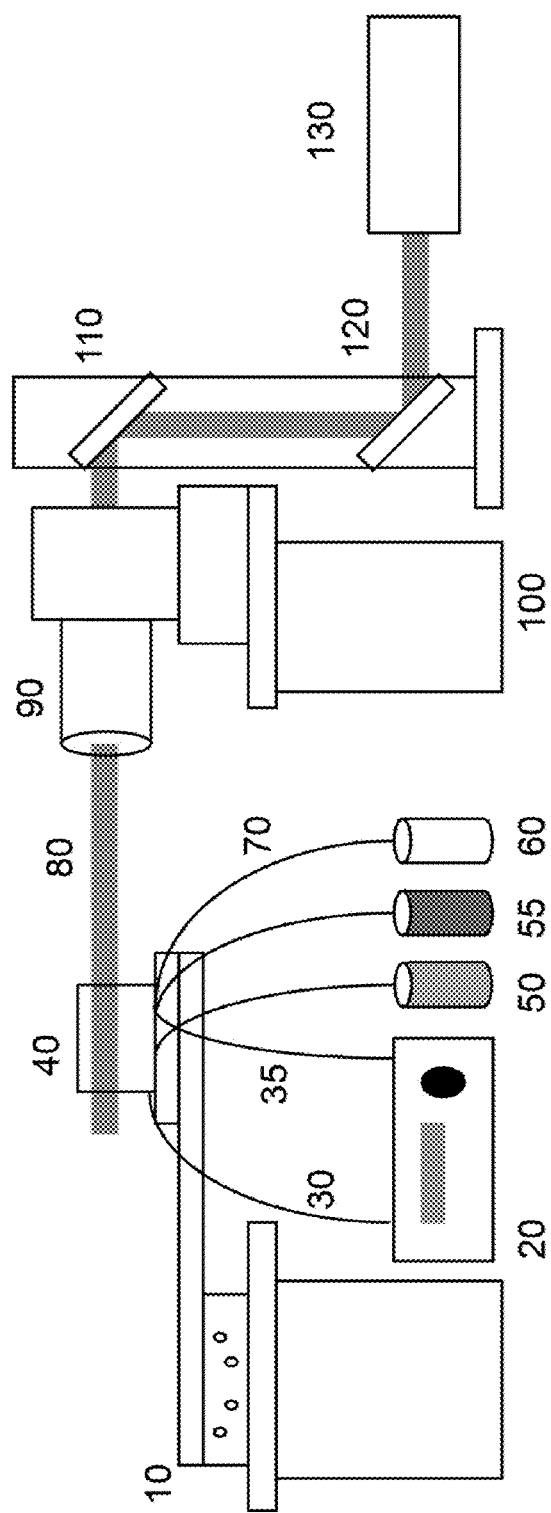
FIG. 1 shows an exemplary device layout.

An exemplary device layout is illustrated in FIG. 1. Of all the components shown, two elements common to most (but not all) geometries and configurations described herein include a source of laser light (130) as well as a source of electrical field (20). The laser source can range in wavelengths from the UV to IR. The electrical sources can have a wide range of voltages in either DC (direct current), AC (alternating current), or mixed format. Each of these components are integrated into a microfluidic platform constructed from glass, plastic, or other materials including combinations of different materials that enable the introduction of laser light into the microfluidic chip (40), without the loss of significant portions of laser power or damage from absorbed wavelengths. The light from the laser source (80) can be directed into the microfluidic chip via mirrors (120, 110) and focusing optics (90) held in place with optomechanical components (100) with the necessary degrees of freedom to direct and align the laser into the microfluidic chip. The microfluidic chip is mounted on optomechanical components (10) that allow all necessary degrees of positional freedom. The electrical source (20) is connected to the microfluidic device via electrodes (30, 35). Fluid flow is fed to the microfluidic chip through several lengths of tubing (70) from up to source volumes (50, 55, 60) and can be regulated with several pumping options including but not limited to syringe pumps, peristaltic pumps, electroosmotic pumps, and pressurized air over liquid pumps. This configuration allows for the elegant combination and study of how optical, fluidic, electrophoretic and/or dielectrophoretic forces simultaneously interact and influence a sample of interest within a custom microfluidic environment.

Counter Laser Field Flow

Figure 2:
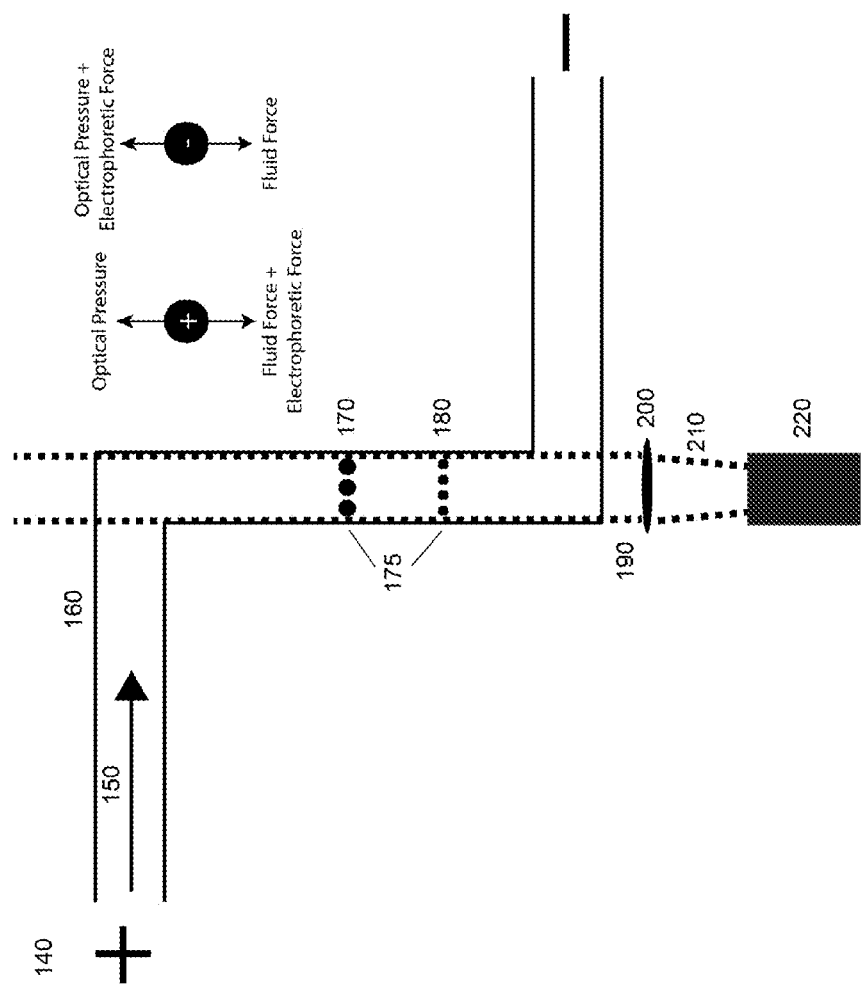
FIG. 2 illustrates an embodiment wherein laser force is countered by fluid flow.

The combination of optical forces countered by flow, such as electroosmotic flow (EOF), within a microfluidic device constitutes the technique known as counter laser field flow. Along the microfluidic channel (160) or capillary the laser propagation (190, 210) is countered by either pure EOF or by a combination of EOF and hydrodynamic flow (150). A detailed illustration of the configuration is shown in FIG. 2 where interrogated samples (170, 180) are separated spatially (175) while being held in equilibrium between the fluidic, electrophoretic and optical forces each sample experiences. Electric field is introduced via electrodes (140). Collimated laser light originates from a source (220) and is focused by an optic (200) into the microfluidic channel where the separation occurs.

The system is capable of trapping and separating various sample types in the channel on the basis of size, shape, refractive index and charge. Particle size can range from several tens of microns to hundreds of nanometers. The addition of electrokinetics to the system of optical chromatography allows for higher resolution separations by adding the ability to probe particle charge as a separable factor.

Co-Directional Laser Field Flow

Detailed is a similar configuration to the Counter Laser Field Flow shown in FIG. 2; however, instead of the laser being directed counter to fluid flow the fluid flow and the direction of laser propagation are in the same direction. In the exemplary illustration of FIG. 3, the laser propagation (270, 290) in the microfluidic channel (250) or capillary is countered by either pure EOF or by a combination of EOF and hydrodynamic flow (240). Interrogated samples (310, 300) become separated spatially (305), while being in equilibrium between the fluidic, electrophoretic and optical forces each sample experiences. Electric field is introduced via electrodes (230). Collimated laser light originates from a source (260) and is focused by an optic (280) into the microfluidic channel (250), where the separation occurs.

Because the particles suspended in the flowing fluid travel in the same direction as the laser propagation, this version of the device does not trap the particulate matter delivered within the main flow. Instead, the position of the particles added to the channel in a batch injection or downstream are separated spatially in the channel and the larger particles (310) equilibrate further downstream than the smaller particles (300). Other samples of similarly sized particles or mixtures of any particles that share the same equilibrium position in a typical optical chromatography device may be separated based completely on surface charge differences (surface charge density, polarity, density, surface area, roughness etc.), a capability not available in traditional optical chromatography.

Orthogonal Laser Field Flow

As seen in FIGS. 4A through 4E, a microfluidic device composed of laser beam (360, 380) orthogonal to central channel (340) containing fluid flow produced by electroosmotic flow or hydrodynamic flow. From a fluidic pinch sample flow (330) the device enables the separation of a mixed sample stream (310) including molecular species and particles having various size/shape/refractive index. The device is capable to continuous high throughput separations when operated using a continuous laser beam (360, 380) and fluid flow, shown in FIG. 4A. Sample introduction (310), pinch flow (330) from a secondary inlet (320), and outlet separation (400 & 410) are generated by having multiple channels connect through a centralized separation/laser region (340). The number of inlets and outlets can each be described by n+1 where n is a whole integer with a 1 or greater value. The interaction (370) of the optical force from the laser allows for the selective removal of particulates from the molecular species stream (400) while also enabling selective positioning of the particles (410) to the various outlets. Collimated laser light originates from a source (350) and is focused by an optic (390) into the microfluidic channel (340), where the separation occurs. This system allows for both the separation of molecular species from particles as well as different particle types from each other. Particles can be isolated from each other on the basis of size, shape, refractive index, and charge.

Figure 4A:
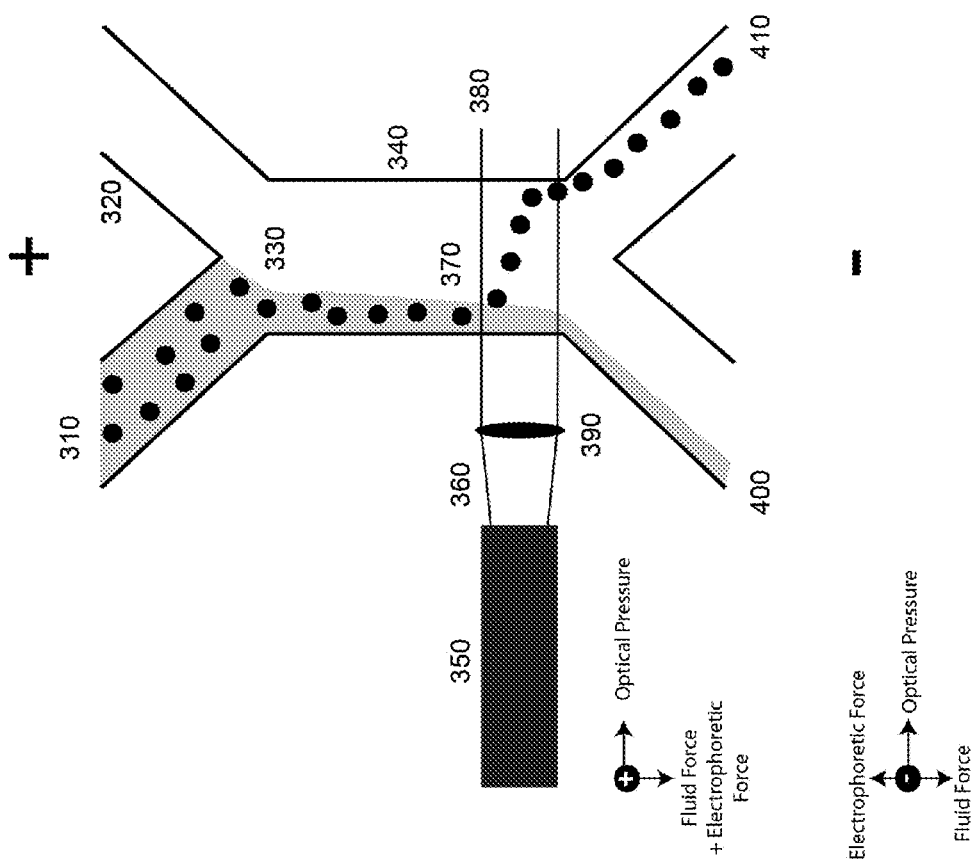
Figure 4B:
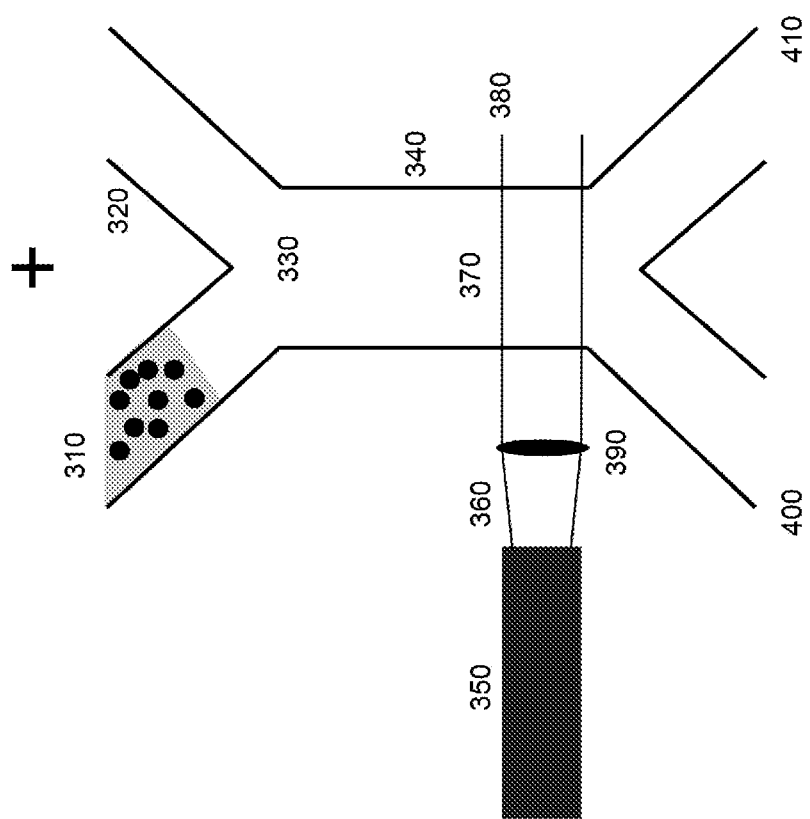
Figure 4C:
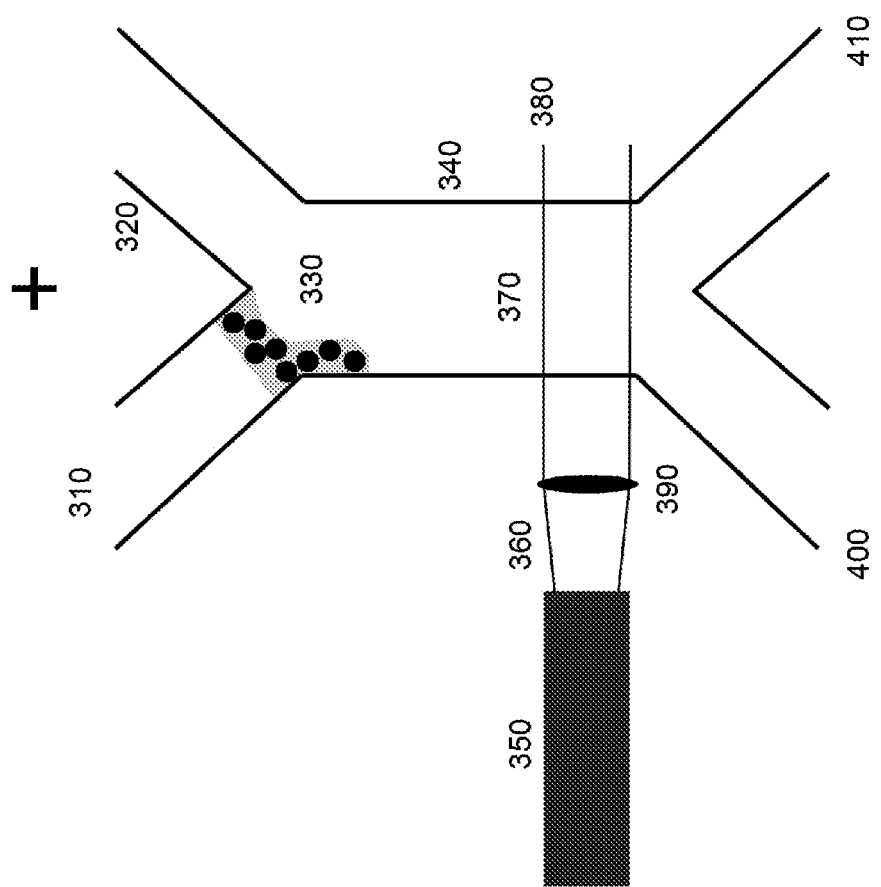
Figure 4E:
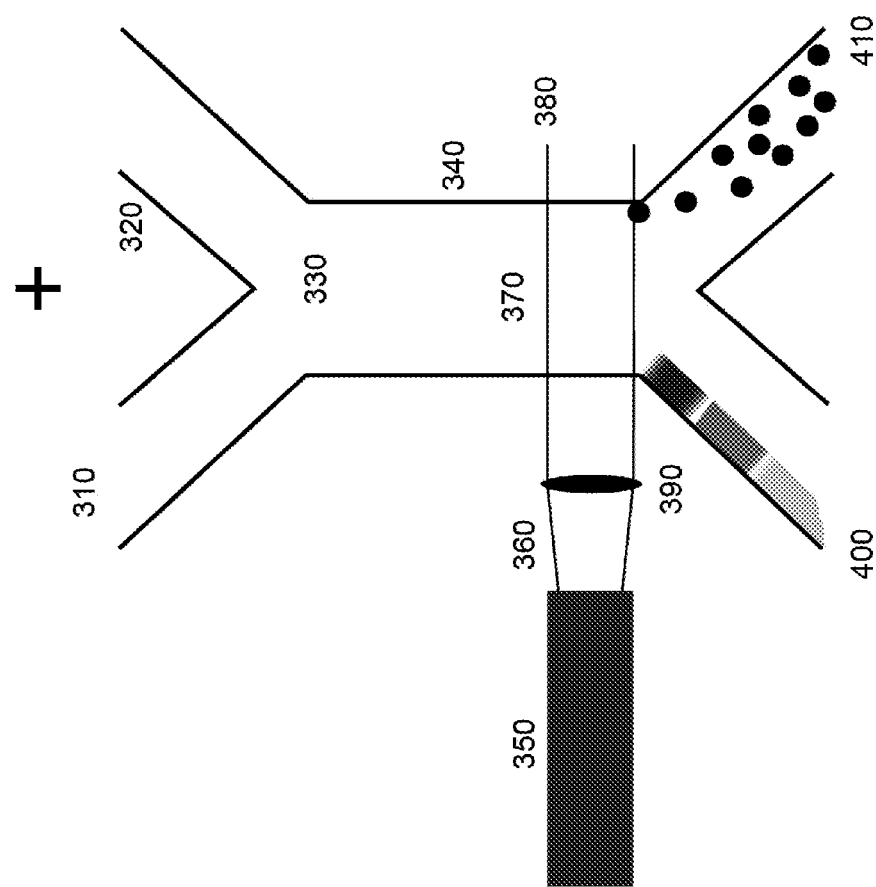

Additional operation modes include the gating of charged molecular species for separating positive or negative molecular components from each other and neutral components as well as particles. FIG. 4B illustrates the stage of sample introduction, with FIG. 4C showing a stage of a gated mode of operation with injection of a plug of charged molecular species. FIG. 4D illustrates the beginning of separation of molecular species from particles during gated operation, with FIG. 4E showing a moment later when such separation is complete.

This preparative separation device can be mated to several traditional analytical detection schemes including but not limited to capillary electrophoresis, spectroscopic investigations, culturing, and antibody studies.

Critical Angle Laser Field Flow

Figure 5:
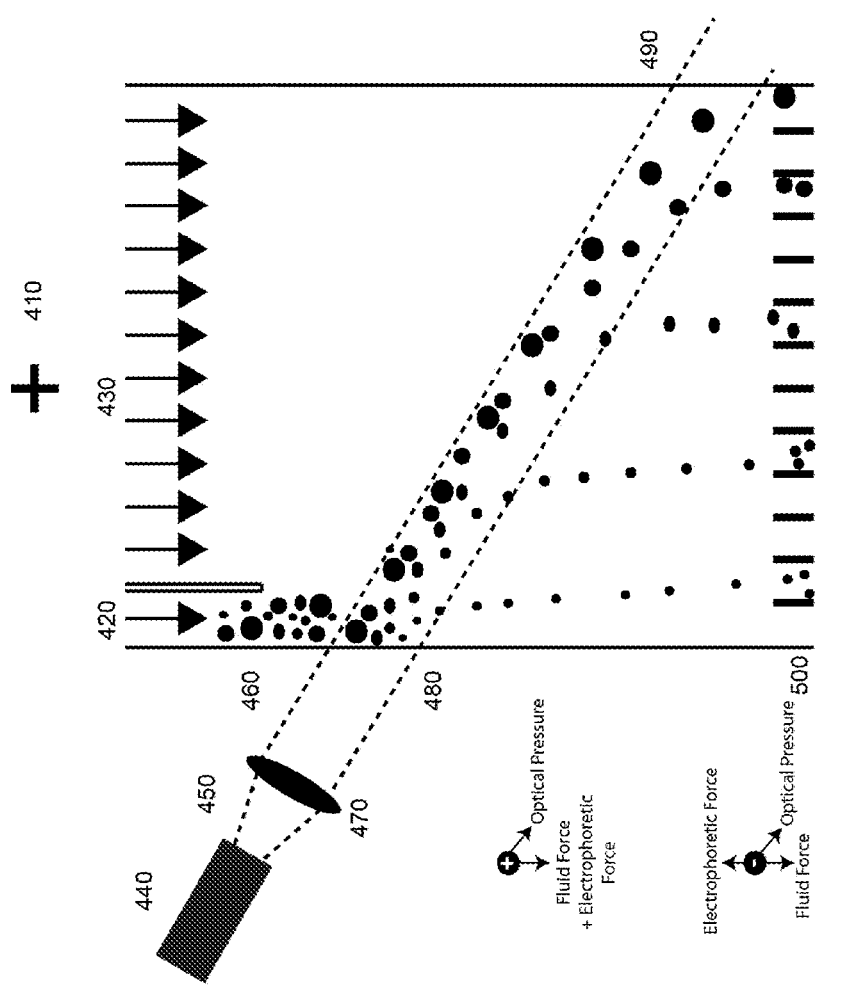
FIG. 5 illustrates an embodiment of critical angle field flow.

FIG. 5 illustrates a microfluidic device utilized to separate a broad size range from tens of nm to several microns by continuously exposing a mixed sized sample stream (420) to an angled continuous laser (490). A laser light source (440) emits laser light (450, 490) that is focused by an optic (470). The angle of the laser (460) is matched to the velocity of the fluid flow (430), for example EOF, in such a manner that the amount of the optical force and the fluid velocity maintain the particle in the laser beam to maximize the residence time of the particle in the beam. EOF is generated using an external electric field (410). A flat flow profile (430) generated via electroosmotic flow while a mixed sample is introduced with the laser beam situated at a critical angle paired to the velocity of the fluid flow. The particles in the mixture will predominantly move in the direction of the laser propagation. Given the critical angle of the beam the force directs the particles away from the sample stream in the same direction as the fluid flow.

As the scattering force scales with particle size and refractive index, larger/higher refractive indices particles will be maintained in the laser beam longer than smaller/lower refractive indexed particles. The critical angle is determined to provide maximum displacement for the largest/highest refractive indexed particle of the group to be separated. Particles will exit the laser beam in a cascading pattern (480) predominately based on their interaction with the laser beam as the electroosmotic flow is not a separative force, but electrophoretic behavior will alter behavior depending on drag and the external field strength. The mixed particle stream will be separated and enriched in separate areas of the main channel (460) as they flow into separate exits (500) at the end of the channel allowing for enriched sub-samples to be collected.

Figure 6:
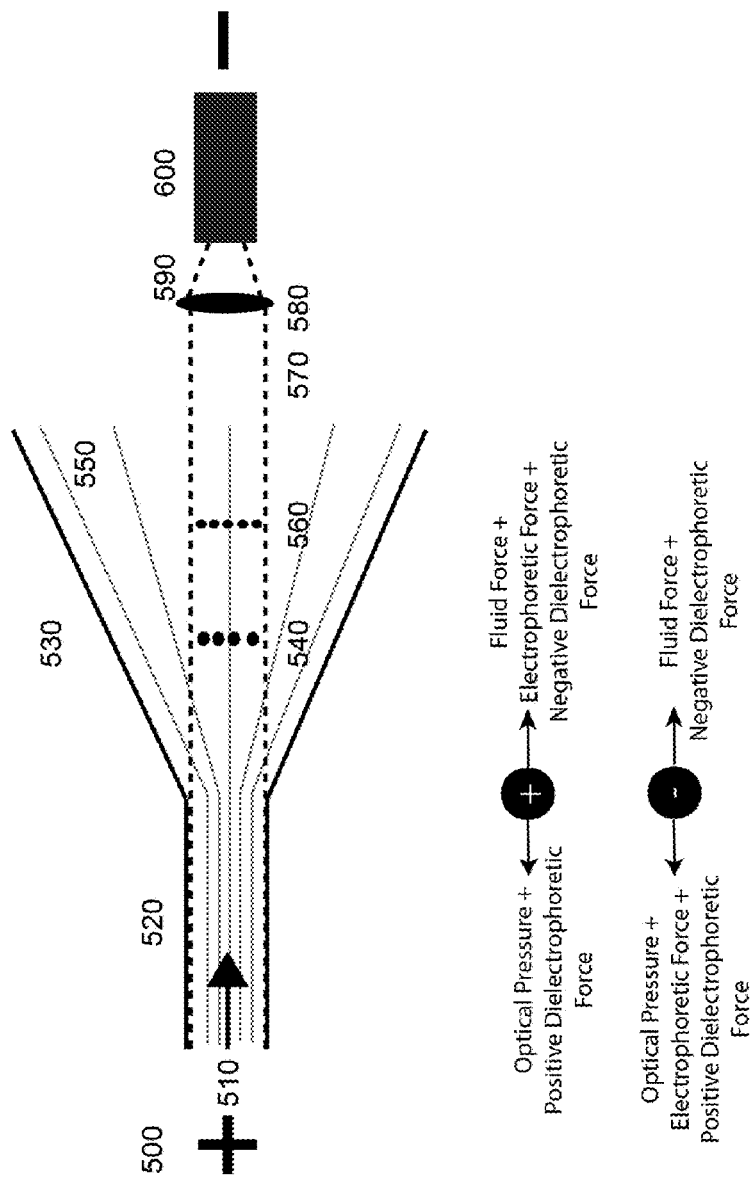
FIG. 6 illustrates an embodiment of dielectrophoretic field flow with a counter-directional laser.
Figure 7:
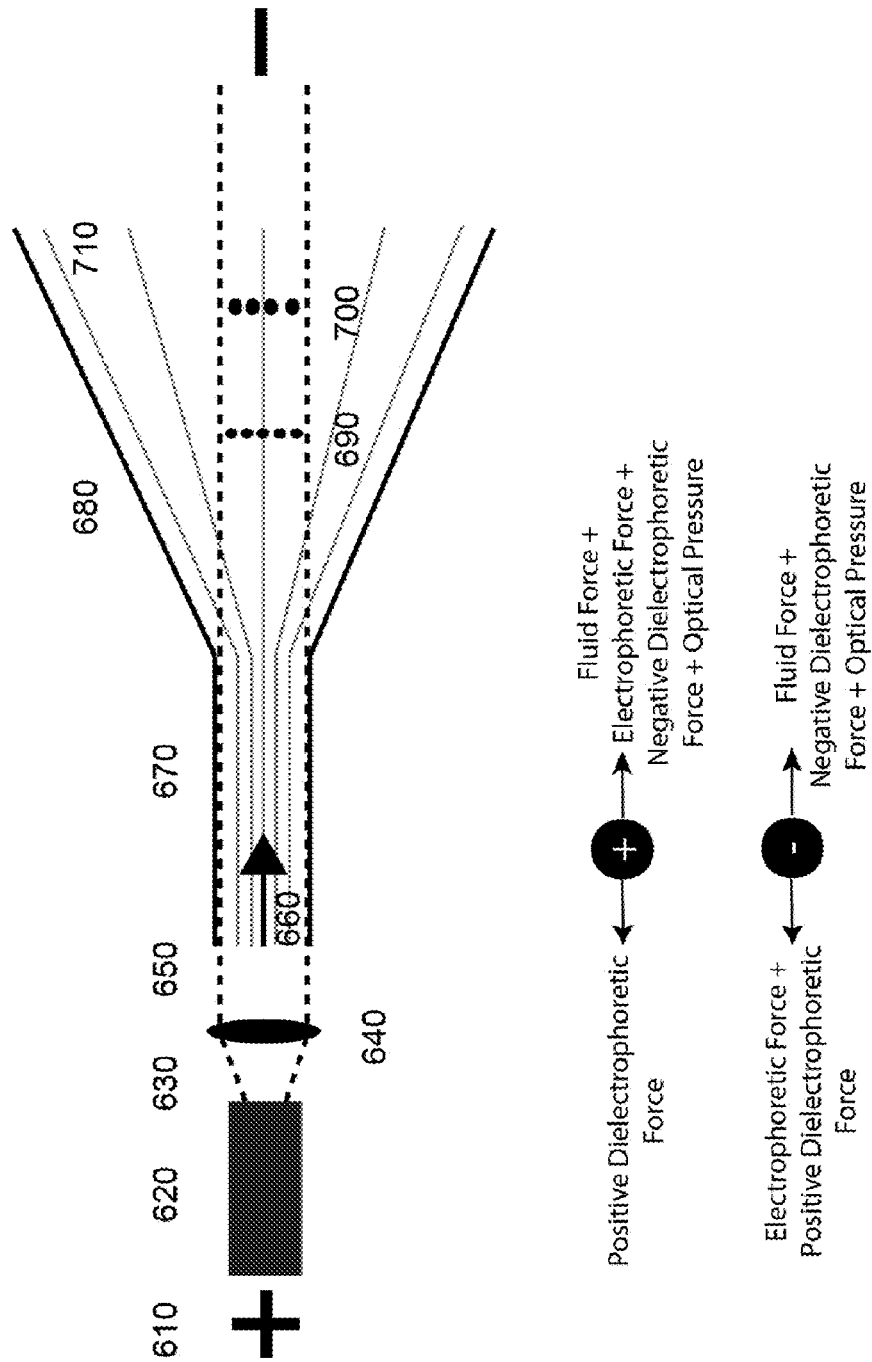
FIG. 7 illustrates an embodiment of dielectrophoretic field flow with a co-directional laser.
Figure 8A:
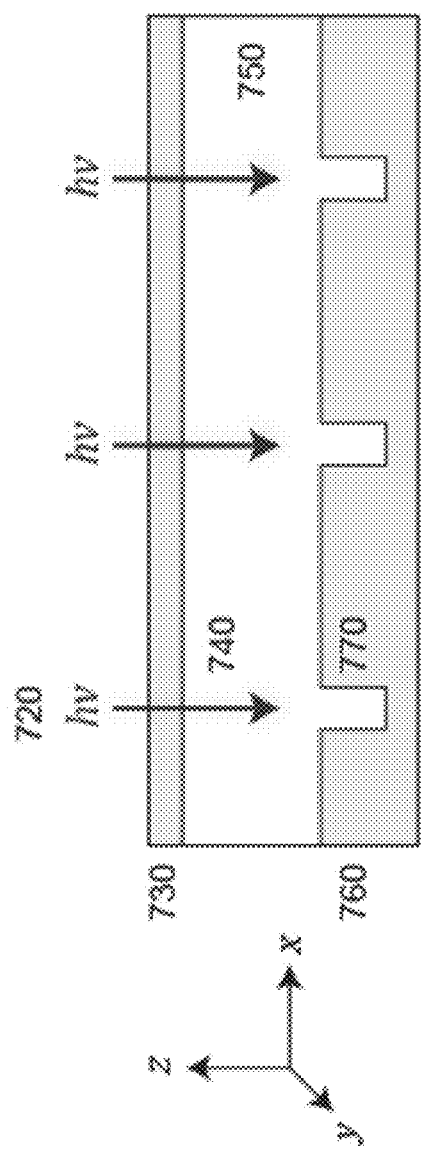
FIGS. 8A and 8B illustrate embodiments of a dielectrophoretic (DEP) trap with an orthogonal laser.
Figure 8B:
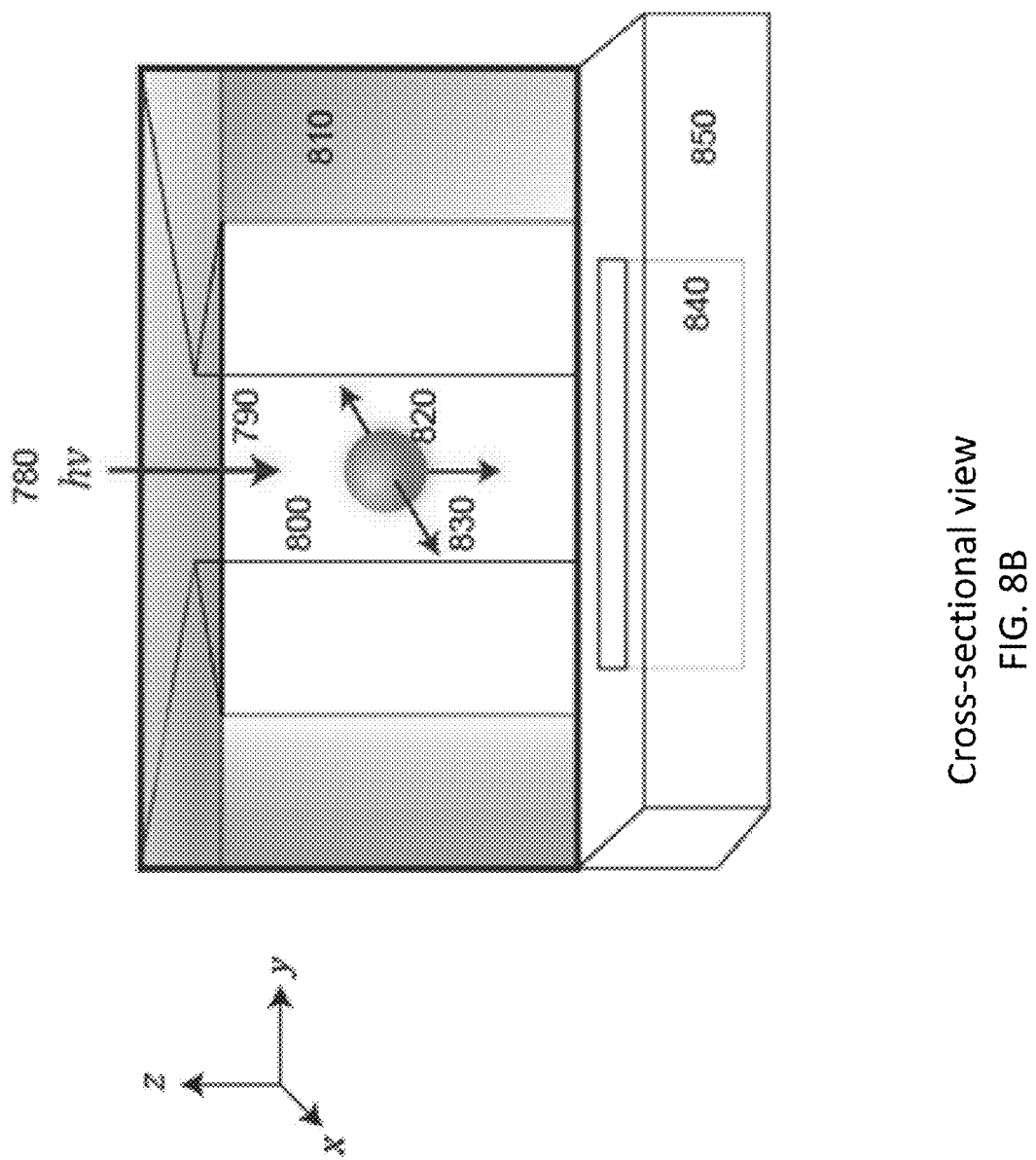
Figure 9:
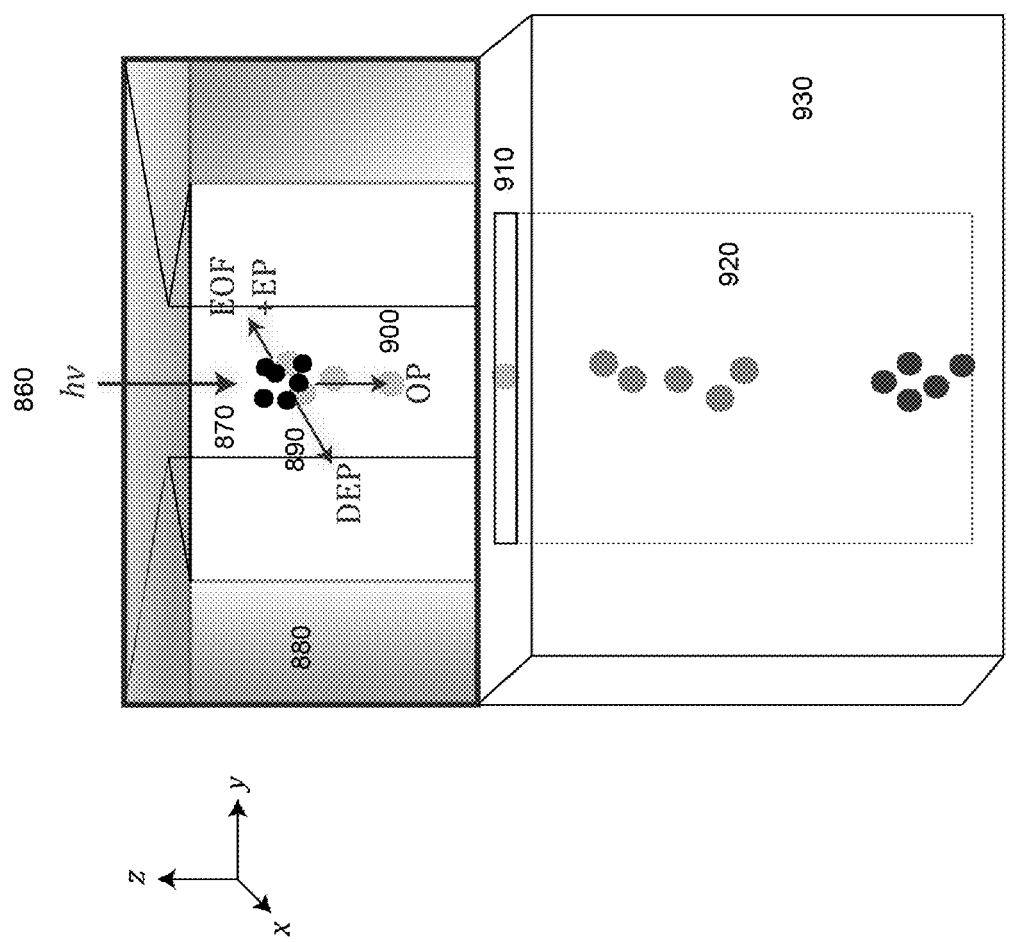
FIG. 9 illustrates one embodiment wherein an optical force acts on particles in a DEP trap.
Figure 10:
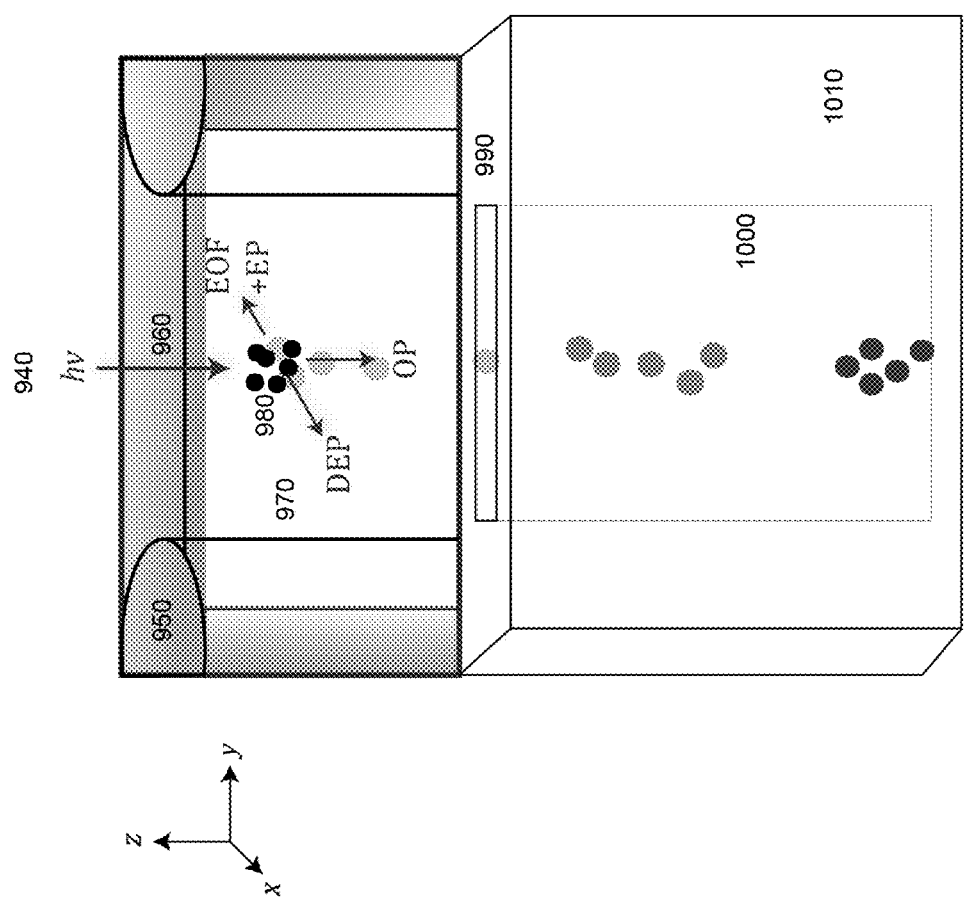
FIG. 10 illustrates a second embodiment wherein an optical force acts on particles in a DEP trap.
Figure 12:
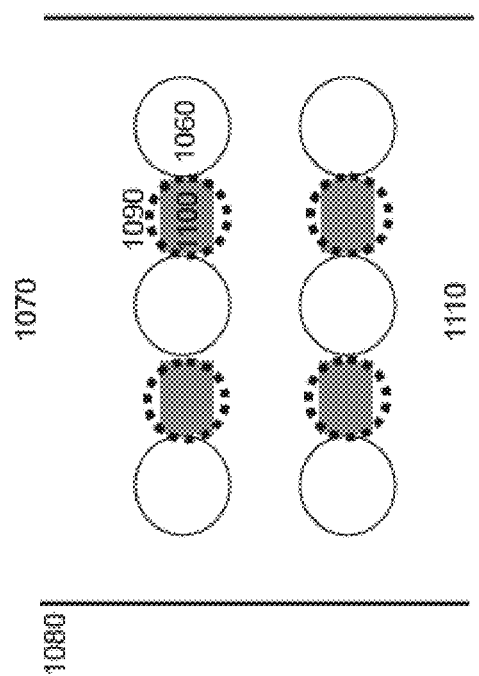
FIG. 12 illustrates a shaped-obstruction embodiment employing a DEP trap.
Figure 11:
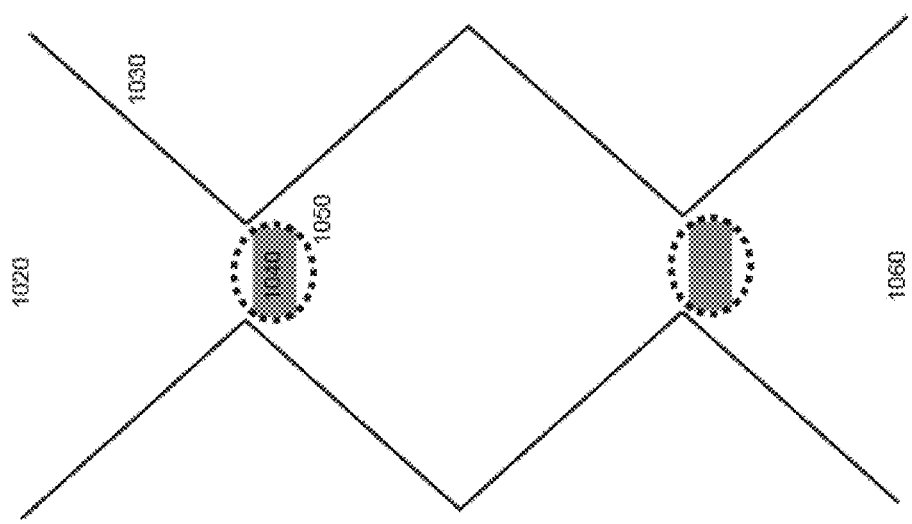
FIG. 11 illustrates a shaped-wall embodiment employing a DEP trap.

This embodiment is similar to the Counter Laser Field Flow method described above, but adds the element of dielectrophoresis (DEP) by shaping the channel to generate a non-uniform electric field (550 & 710). This combination can be utilized to separate a mixed population of particles (540, 560, 690, & 700) via their DEP and optical properties. The optical force can be applied either counter to the EOF or pressure induced flow (510 & 660) for the purposes of trapping or velocity monitoring various particle types (540 & 560), or can be used co-directionally with the EOF for sorting and velocity monitoring of various types of particles (690 & 700). Electric fields (500 & 610) can be DC or AC or mixtures of the two. DEP field can be any linear or non-linear function of DEP generated by the channel (530 & 680). As seen in FIGS. 6 and 7, the laser is introduced to axially to the channel in either a co-directional (630 & 650) or counter direction (570 & 590) with regard to fluid flow (510 & 660). Collimated laser light originates from a source (600 & 620) and is focused by an optic (580 & 640) into the microfluidic channel (520 & 670), leading to the shaped channel geometry where the separation occurs.

Dielectrophoretic Trap Orthogonal Laser Manipulation & Separation

DEP traps (820) are utilized to generate populations of separated particles isolated on the basis of their electrokinetic properties (830), as illustrated in FIGS. 8 through 12. These separated populations of particles can in turn be probed by optical forces (720, 740, 780, 790, 860, 940) from a laser to explore other separation vectors, like refractive index. Additionally, the optical force can be ramped in order to gauge the strength of the trap, selectively "elute" heterogeneous particles from the population (890 & 980), or to move the particles from the trap toward other channels (770 & 840) for further applications. An exemplary device consists of an open microfluidic channel (750, 800, 870, 970, 1020, 1070, 1110) constructed with a single or a series/array of DEP traps (810) that allow for fluid flow orthogonal to a laser (720 & 780) that enters above trapped particle populations through a suitable portion of the channel wall (730, 960) and potential well or other channel structures (840) that may be positioned in an opposing channel wall (760, 850, 930, 1010). The DEP trap could be made through either insulator or electrode based systems. Insulator DEP systems can generate non-uniform field could be shaped wall geometries (880 & 1030) or obstruction geometries (950 & 1060) of any shape, e.g. round, elliptical, square, diamond, teardrop, and triangular columns.

The addition of the optical force allows for the controlled movement, manipulation, and separation of a plurality of particles (890 & 980) that have been trapped/collected in a DEP trap (880 & 950). The selective movement of these particles based on size, shape, and refractive index into an adjoining channel structure (910, 920, 990,1000) allows for further processing of the particles and collection for use. From a vantage point above the microfluidic channel the shaped wall (1030) or the shaped obstructions (1060) with a straight side wall (1080) are visible as are the well or channel shunt features (1040 & 1100) with the laser beam (1050 & 1090) outline also being visible over the well/channel features at each structure.

Dielectrophoretic Velocity Monitoring for Identification And Sorting

Figure 13:
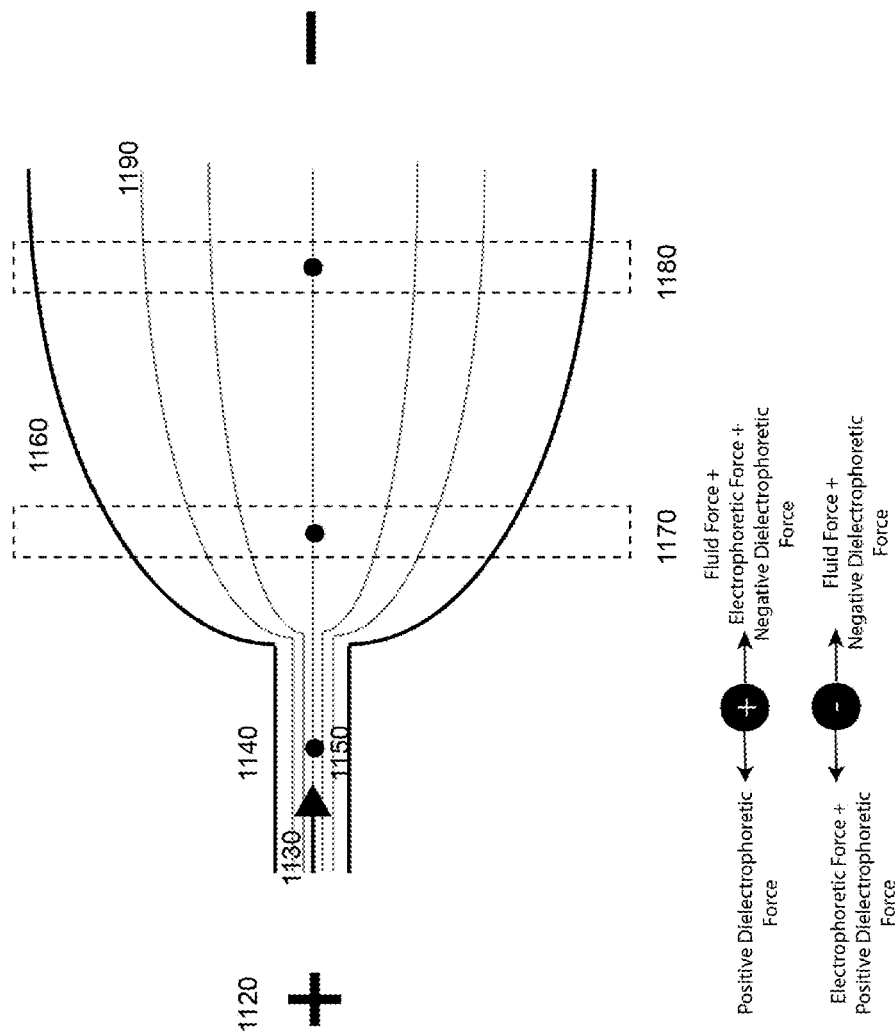
FIG. 13 illustrates an embodiment of DEP velocity modification.
Figure 14:
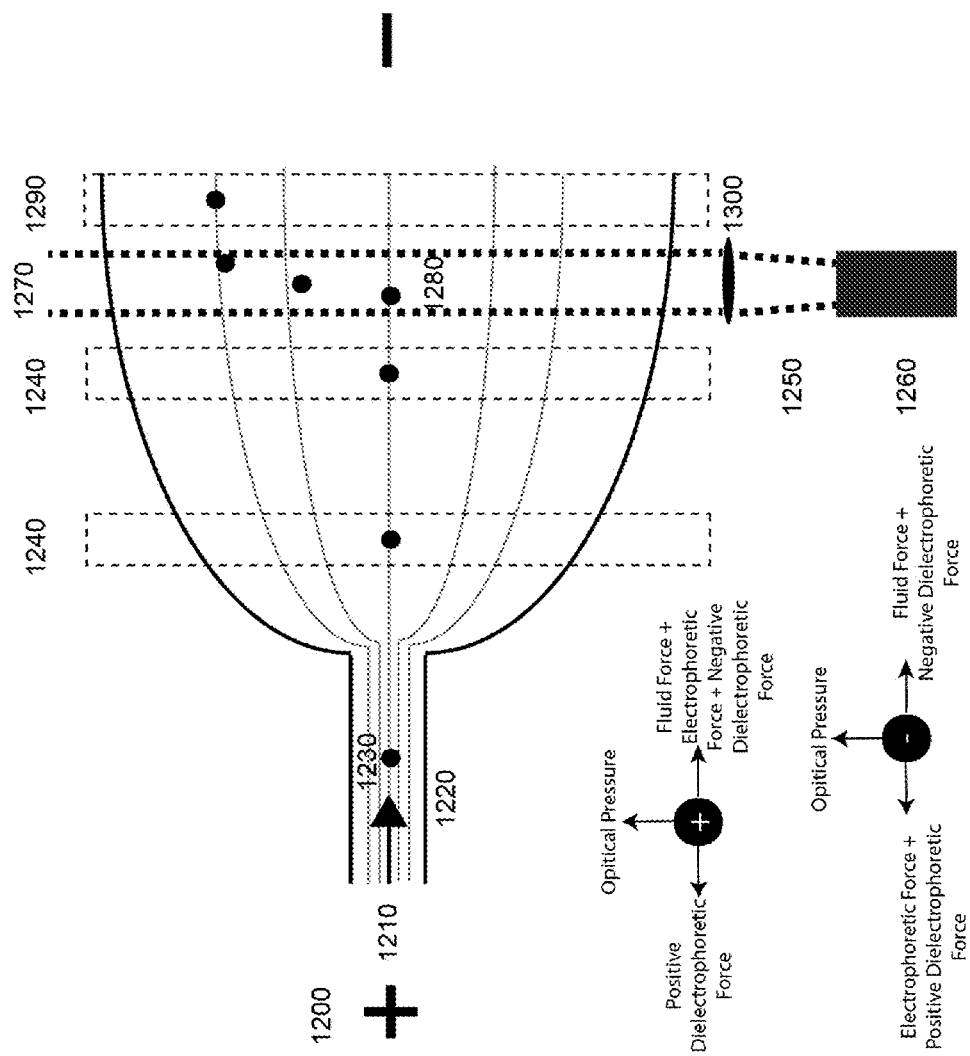
FIG. 14 illustrates an embodiment of DEP velocity modification with optical force deflection.

As shown in FIG. 13, a microfluidic channel (1140 & 1160) generates either a linear or non-linear DEP field (1190) that allows particles (1150) to pass through the middle of the channel while allowing the effect of the field on the particles' velocity (acceleration, deceleration, or neutral) to be observed. The DEP field is generated via the combination of an external electric field (1120) and the shaped channel wall (1160). Fluid flow (1130) can be either EOF or pressure induced flow, thus enabling the device to be manufactured in either EOF supporting material or simply non-conductive materials. The effect on the velocity of the particle allows the viewer to understand the polarization, charge, and permeability of the particle to be determined in a high-throughput fashion. The particle is view in the first region of interest (ROI) (1170) and then again in the second ROI (1180) to determine velocity. This system allows for identification, sorting, and manipulation when combined with switching and collection. Dielectrophoretic Velocity Monitoring for Cell Identification and Sorting with Optical Force Deflection Building on the previous embodiment, FIG. 14 illustrates a technique whereby adding an orthogonal optical force (1270) component allows the system to act like a 2-D gel, reporting information from DEP in addition to the refractive index from the optical force interaction (1280). Again, an external electric field (1200) generates a DEP field through its being shaped by the geometry of the insulating channel wall (1220). Fluid flow (1210) can be either EOF or pressure induced flow, thus enabling the device to be manufactured in either EOF supporting material or simply non-conductive materials. A source of laser light (1260) produces a laser beam (1250) which in turn is focused by an optic (1300) into the channel. After the particles (1230) are successively introduced to the channel (1220) via fluid flow (1210) the particle interacts with the DEP field and their velocity is calculated as the particle passes through regions of interest (ROI) 1 and 2 (1240). Then the particle stream passes into the laser beam (1270) and are displaced from their original trajectory (1280). As the particle passes through ROI 3 (1290) the amount of displacement is quantified. This displacement is informational as the particle's refractive index, shape, and size. The placement of the laser in the channel system can occur along curved and straight portions of the channel.

Advantages and Applications

The possibility of separating chemically different particles offers important new possibilities for analysis and possible purified collection of colloidal samples such as organic particulates, inorganic particles (glass and metal particles), and biological species such as cells, bacteria, and viruses. Other samples may also be used, including but not limited to carbon nanotubes, quantum dots (including single, dimer & trimer forms), vesicles, organelles, samples relating to in-vitro fertilization (IVF), and liposomes.

These techniques may be used to distinguish and/or diagnose any number of characteristics in samples, for example:

Live v dead organisms
Presence or absence of antibodies
Cell cycle stage
Blood cells types (e.g., red blood cells, white blood cells, platelets)
Cancer
Infected cells, including cells infected with virus, bacteria, or parasites (e.g., malaria or giardia)
Abnormal cells The techniques may be used with, against, or neglecting gravity; in an array; or in multiple passes.

The techniques may be used to distinguish many particles traits such as:

Shapes (including spherical or odd shapes)
Presence or absence of coatings
Absorbing and non-absorbing wavelength
Tagged and tag-less
Sorting particles of interest selectively from a plurality of particles
Sorting particles from chemical or biochemical mixtures Furthermore, as contemplated by one of skill in the art, it is possible to use various laser types having any suitable beam geometry and type.

The systems described herein highlight the ability to separate particles (including but not limited to biologics such as cells) from chemical or biochemical (e.g., protein or other) molecular species using a mixed optical force and electrophoretic or dielectrophoretic force combination. This capability represents a significant leap forward in a technology platform that could be used for combined chemical/biochemical and biological analysis and sorting. The implications are far reaching, as a combined system capable of doing both chemical and biological warfare agent detection does not yet exist.

Differentiation of biological samples such as bacteria is traditionally based upon chemical differences in their capsules, membranes or other surface or sub-surface features. Polysaccharides, lectins, lipoteichoic acids, and proteins are some of the biomolecules present in various bacterial species and strains. It is well known that there exists a substantial range of refractive indices in bacterial and viral samples due to their different chemical compositions. The ability to separate biological species based upon physical and chemical properties using only light interaction with samples in a simple fluid flow is new and has great potential benefits when applied to bio-warfare detection and biomedical analysis. Not only are samples physically separable using light, but from their position in the separation field one can determine their unique intrinsic characteristics that will allow separation from one another either actively or passively.

The ability to distinguish and sort one cell type from another is predicated on force differences significant enough to generate physical space between the particles. In a microfluidic device, this generally means tens of microns of spatial separation are required at a minimum. Having an orthogonal forces working in tandem to effect a separation is advantageous over either single force alone. While the electrophoretic force is sensitive to surface charge, the optical force is sensitive to the overall refractive index of the particle and indeed local optical variations within the cell or on the surface. Thus, the forces are sensitive to fundamentally different phenomena. The combination of electrophoretic or dielectrophoretic forces and optical force will be a powerful combination that will allow much finer separations to be achieved in a single instrument.

Other Techniques

Free from the requirements of chemical or immunological systems, a technique based upon optical separation and detection alone will outperform the current levels of performance achieved using other methods. Systems based upon immunology require significant time and cost outlays to develop antibodies for new biological warfare (BW) agents (ref. 1). Furthermore, with these techniques, the detection of modified and/or unknown species in real time is not possible. Other techniques based upon DNA analysis, while very accurate, have problems including long analysis times, high cost and complexity, and delicate instrumentation which is unlikely to be reduced in size significantly. Other methods of BW agent detection include fluorescence detection of aerosols (ref. 2). Such techniques are limited in their ability to detect BW agents, as intrinsic fluorescence is derived from three amino acids (with similar excitation and emission spectra) common to many biological particles. Detection based upon fluorescence alone is not likely to enable characterization of closely related species.

Field flow fractionation (FFF) is used for the separation of particulate materials based upon their size, mass, density, charge, or other physical properties (refs. 3 and 4). The most basic variant of FFF uses a flow field to carry particulates in flow down a thin channel. These particles are then subjected to a force (gravitational, flow, electrical, or other) that causes them to accumulate differentially at the wall edge of the laminar flow field. Particles least affected by the applied field will travel down the channel and exit sooner than those that are more effected by the applied field. Recently, strains of E. coli have been separated using a variation of FFF based upon the presence or absence of fimbriae (ref. 5).

Flow cytometry is a technique used for characterizing cell populations wherein a sheath flow fluidic system hydrodynamically focuses the cells into a line (refs. 6 and 7). Once in a line, the stream containing the cells is interrogated by one or more laser beams of differing wavelength. Laser light scattering and laser induced fluorescence (for dye labeled particles or cells) measurements are made of the passing samples. From these, many parameters can be determined including size, volume, granularity, and biochemical properties using dye labeled cell surface antigens. In a cell sorting flow cytometer, after the optical measurements, the sheath flow is vibrated at a high velocity creating tiny droplets, which ideally contain only one cell. Depending on the cell type determined by the laser measurements, a charge is applied to the droplets. When these charged droplets pass between two charged plates they are deflected and can be collected, resulting in a specifically directed separation.

While the above techniques enable separation, they suffer limitations that the current invention alleviates. Discrimination is not inherently based upon intrinsic chemical composition when using field flow fractionation. This limits the technique to essentially size based separation which are not as universally important as biochemical specificity when dealing with microbiological samples. With respect to flow cytometry, sorting can be achieved based upon physical properties and biochemical information derived from specific fluorescent probes. While being a powerful bioanalytical technique, flow cytometry suffers from the cost and complexity of the fluid system and the multiple color lasers required to excite fluorescence in dye labeled biochemical markers. More importantly, much biochemical specificity and identification are achieved through the use of bioprobes, which by definition require prior knowledge for successful application. A method such as optical laser separation which relies on the intrinsic characteristics of the biological species should prove more versatile and capable.

Optical trapping has been used for the repetitive sorting of particles based on their appearance, including size, shape, or other visible features. Recently, more sophisticated and automated optical techniques have been identified and developed to separate microscopic objects (refs. 9 and 10). These techniques involve arrays of optical traps in a fluid flow to preferentially transport microscopic objects that experience a greater optical force away from those that experience a lesser force.

Electrophoretic mobility has been used to sort cells, bacteria and other particles based upon size and charge ratios for some time (ref. 11). Electrophoresis is based on the surface charge of a particle or charged molecular species exposed to electrostatic forces generating a force on the particle or molecular species that drags it toward the oppositely charged pole of the field. This is described by the electrophoretic mobility ($\mu e$) being equal to the charge (q) divided by the viscous term ($6r\pi\eta$, r is the radius of the species, and $\eta$ is the viscosity of the medium). The migration velocity (ve) of the species is derived by multiplying $\mu e$ by the electric field strength (E). This simple description is valid for molecular species. The charged walls of the fluidic device can also cause an additional electrokinetic phenomena known as electroosmotic flow (EOF) that generates bulk fluid flow.

Dielectrophoresis is a complex phenomenon where an electric field gradient interacts with dipoles and other multipoles properties of molecules and particles and elicits movement or trapping behavior (ref. 12). The DEP was first described by Pohl in 1951, which presented a theoretical explanation for the force and detailed its use for removing suspended particles from polymer solutions(ref. 13). Subsequently DEP has been adapted and applied to a wide variety of biological structures such as cells, spores, bacteria, and viruses (ref. 14). Unlike electrophoresis, which acts primarily on the charge-to-size ratio of the particle, DEP acts on a larger set of properties including polarizability, structure and medium permeability, and charge/charge distribution. As a result higher resolution separations and greater sensitivity is often observed in DEP separations. Researchers using DEP have achieved impressive results including separating cancer cells from blood cells, (ref. 15) infected cells from normal cells, (ref. 16) and live from dead cells (ref. 17).

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. F. S. Ligler, G. P. Anderson, P. T. Davidson, R. J. Foch, J. T. Ives, K. D. King, G. Page, D. A. Stenger, and J. P. Whelan, "Remote Sensing Using an Airborne Biosensor", Environ. Sci. Technol., 1998, 32, 2461-2466.
2. N. F. Fell, et al., "Concentration, Size, and Excitation Power Effects on Fluorescence from Microdroplets and Microparticles Containing Tryptophan and Bacteria", SPIE Vol. 3533, 52, 1999.

3. T. Chianea, N E. Assidjo, P. J. P. Cardot, "Sedimentation Field Flow fractionation: Emergence of a new Cell Separation Methodology", Talanta, 51, 835-847, 2000.
4. K. G. Wahlund, and J. C. Giddings, "Properties of an Asymmetrical Flow Field Flow Fractionation Channel Having One Permeable Wall", Anal. Chem., 59. 1332-1339, 1987.
5. P. Reschiglian, A. Zattoni, B. Roda, S. Casolari, M. H. Moon, J. Lee, J. Jung, K. Rodman, " Bacteria Sorting by Field Flow Fractionation. Application to Whole-Cell *Escherichia coli* Vaccine Strains", Anal. Chem., 74, 4895-4904, 2002.
6. Gilman-Sachs, "Flow Cytometry", Anal. Chem., 66, 13, 1994.
7. J. W. Hofstrat, W. J. M., van Zeijl, J. C. H., Peeters, and L. Peperzak, "Flow Cytometry: Fast and Quantitative Characterization of Particles in Suspension", Anal. Chim. Acta., 290, 135-145, 1994.
8. Oakey, J.; Allely, J.; Man, D. W. M. Biotechnology Progress 2002, 18, 1439-1442.
9. Korda, P. T.; Taylor, M. B.; Grier, D. G. Physical Review Letters 2002, 89.
10. MacDonald, M. P.; Spalding, G. C.; Dholakia, K. Nature 2003, 426, 421-424.
11. Meighan, M. M., Staton, S. J. R., Hayes, M. A., Electrophoresis 2009, 30, 852-865
12. Subirats, X., Blaas, D., Kenndler, E., Electrophoresis 2011, 32, 1579-1590.
13. Pohl, H. A., Dielectrophoresis, Cambridge University Press, Cambridge 1978.
14. Pohl, H. A., Journal of Applied Physics 1951, 22, 869-871.
15. Chin, S., Hughes, M. P., Coley, H. M., Labeed, F. H., International Journal of Nanomedicine 2006, 1, 333-337.
16. Pethig, R., Critical Reviews in Biotechnology 1996, 16, 331-348.
17. Pysher, M. D., Hayes, M. A., Analytical Chemistry 2007, 79, 4552-4557.

The invention claimed is:

1. A method of separating particles in a microfluidic channel, the method comprising:
   providing a device comprising a microfluidic channel, a source of laser light focused by an optic into the microfluidic channel, and a source of electrical field operationally connected to the microfluidic channel via electrodes;
   flowing particles in a liquid through the microfluidic channel; and
   manipulating the laser light and the electrical field to act jointly on the particles in the microfluidic channel, thereby separating the particles based on size, shape, refractive index, electrical charge, electrical charge distribution, charge mobility, permittivity, and/or deformability,
   wherein the electric field is generated by electrodes positioned at inlet and outlet ends of the channel and beyond a region of the microfluidic channel where particle separating occurs.

2. The method of claim 1, wherein the flowing is electroosmotic and/or pressure driven.

3. The method of claim 1, wherein a force imparted by said laser light is countered by fluidic flow in said microfluidic channel.

4. The method of claim 1, wherein a force imparted by said laser light is in the same direction as fluidic flow in said microfluidic channel.

* * * * *